(12) United States Patent
Schaefer et al.

(10) Patent No.: US 10,941,156 B2
(45) Date of Patent: Mar. 9, 2021

(54) CYCLIC KETALS AS FRAGRANCE PRECURSOR COMPOUNDS

(71) Applicant: Henkel AG & Co. KGaA, Duesseldorf (DE)

(72) Inventors: Sascha Schaefer, Mettmann (DE); Silvia Sauf, Velbert (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/421,938

(22) Filed: May 24, 2019

(65) Prior Publication Data

US 2019/0276469 A1    Sep. 12, 2019

Related U.S. Application Data

(63) Continuation of application No. PCT/EP2017/079608, filed on Nov. 17, 2017.

(30) Foreign Application Priority Data

Nov. 25, 2016   (DE) ........................ 10 2016 223 412

(51) Int. Cl.
| | | |
|---|---|---|
| *A61K 8/18* | (2006.01) | |
| *A61Q 13/00* | (2006.01) | |
| *A61K 8/00* | (2006.01) | |
| *C07D 493/20* | (2006.01) | |
| *C07D 317/20* | (2006.01) | |
| *C11B 9/00* | (2006.01) | |
| *C11D 3/20* | (2006.01) | |
| *A01N 43/90* | (2006.01) | |
| *C11D 3/50* | (2006.01) | |
| *C07D 317/08* | (2006.01) | |

(52) U.S. Cl.
CPC .......... *C07D 493/20* (2013.01); *A01N 43/90* (2013.01); *A61Q 13/00* (2013.01); *C07D 317/08* (2013.01); *C07D 317/20* (2013.01); *C11B 9/0076* (2013.01); *C11B 9/0088* (2013.01); *C11D 3/2096* (2013.01); *C11D 3/50* (2013.01)

(58) Field of Classification Search
CPC ..... C07D 493/20; C07D 317/20; C11B 9/088; C11B 9/0076
USPC ...................................... 512/9, 8, 1
See application file for complete search history.

(56) References Cited

U.S. PATENT DOCUMENTS

| | | | |
|---|---|---|---|
| 2009/0069416 A1* | 3/2009 | Miura | A61K 8/4973 514/467 |
| 2014/0147395 A1 | 5/2014 | Rieth et al. | |
| 2017/0188584 A1* | 7/2017 | Jabs | A01N 63/00 |

FOREIGN PATENT DOCUMENTS

| | | |
|---|---|---|
| DE | 19718537 A1 | 11/1998 |
| WO | 9734986 A1 | 9/1997 |
| WO | 9734989 A1 | 9/1997 |
| WO | 01085713 A1 | 11/2001 |
| WO | 2014047428 A1 | 3/2014 |
| WO | 2014183883 A1 | 11/2014 |

OTHER PUBLICATIONS

Zhao et al, Practical Synthesis of an L-Fructose-Derived Ketone Catalyst for Asymmetric Expoxidation of Olefins, Feb. 16, 2006, J. Org. Chem., 71, 5377-5379 (Year: 2006).*
Quiclet-Sire et al, A practical modification of the Barton-McCombie Reaction and Radical O- to S-Rearrangement of Xanthates, 1998, Tetrahedron Letters, 39, 9435-9438 (Year: 1998).*
Biela-Banas et al, A reinvestigation of synthesis and revision of spectral data of 1,2-O-isorpropylidene-alpha-L-sorborfuranose, 1,2:4,6-di-O-isopropylidene-alpha-L-sorbofruanose and derivatives, 2013, Carbohydrate Research, 380, 23-28 (Year: 2013).*
International Search Report PCT/EP2017/079608 Completed: Feb. 20, 2018, dated Apr. 23, 2018 2 pages.

* cited by examiner

*Primary Examiner* — Jessica Whiteley
(74) *Attorney, Agent, or Firm* — Bojuan Deng

(57) ABSTRACT

The invention is directed to the field of pro-fragrances used in detergents and cleaning agents, cosmetic agents and air fresheners, for example. The invention relates to particular cyclic ketals used as pro-fragrances. The invention also relates to detergents and cleaning agents, cosmetic agents and air fresheners containing ketals of the type. The invention further relates to a method for creating a long-lasting fragrance on surfaces and for repelling insects.

9 Claims, No Drawings

CYCLIC KETALS AS FRAGRANCE PRECURSOR COMPOUNDS

FIELD OF THE INVENTION

The present invention relates to the field of pro-fragrances, as used, for example, in the field of washing or cleaning agents, cosmetic agents and air care agents. The invention relates to specific cyclic ketals that function as pro-fragrances. The present invention further relates to washing and cleaning agents, cosmetic agents and air care agents containing ketals of this kind. The invention further relates to a method for long-lastingly fragrancing surfaces.

BACKGROUND OF THE INVENTION

Washing and cleaning agents and cosmetic agents usually contain fragrances that impart a pleasant odor to the agents. The fragrances usually mask the odor of the other ingredients, thus giving the user a pleasant impression in terms of odor.

In particular in the field of washing agents, fragrances are important components in the formulation, since it is intended for both damp laundry and dry laundry to have a pleasant, fresh fragrance. A basic problem associated with the use of fragrances is that they are more or less highly volatile compounds, although a long-lasting fragrance effect is desired. In particular in the case of odorants that produce the fresh, light notes of the perfume and evaporate particularly quickly due to their relatively high vapor pressure, it is difficult to achieve the desired long-lasting impression of fragrance. Pro-fragrance molecules, which are for example hydrolysis or photolabile pro-fragrance molecules, are known in the prior art, and represent one option for the delayed release of fragrances. The effect of environmental factors causes splitting of a covalent bond in the pro-fragrance molecule, thereby releasing a fragrance.

Ketals are known in the prior art as fragrances and fragrance precursors, referred to as pro-fragrances. Ketals as fragrances are disclosed, for example, in the international application WO 2014/183883 A1. The cyclic ketals described therein have a direct effect as fragrances having an ambergris scent. Fragrance precursors which release the actual fragrance molecule by hydrolysis of the ketals are not mentioned, however.

The international applications WO 97/34986 A1 and WO 97/34989 A1 describe acetals and ketals as fragrance precursors, for example for use in washing agents. The ketals described are structurally different from those described in this document.

The international application WO 01/85713 A1 describes cyclic ketals as fragrance precursors of acetophenones.

Finally, the German application DE 19718537 A1 also describes depot preparations intended for the targeted release of fragrance and obtainable by reacting fragrance aldehydes or ketones with polyhydroxy compounds.

However, when well-known pro-fragrance molecules are used, the fragrance intensity is low and the fragrance effect has only a short duration. Therefore, there is also a need for alternative pro-fragrance molecules that effectively release fragrances and have a sufficiently high fragrance intensity.

It was surprisingly found that specific cyclic ketals of formula (I) are suitable, under slightly acidic conditions, for effectively releasing fragrances and thus having a higher fragrance intensity than ketals known from the prior art.

BRIEF SUMMARY OF THE INVENTION

In a first aspect, the present invention is therefore directed to compounds of formula (I)

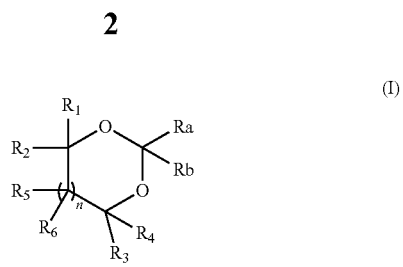

wherein
Ra and Rb, together with the C atom to which they are bonded, are a linear, branched or cyclic, substituted or unsubstituted hydrocarbon functional group having 6 to 30, preferably 6 to 20, carbon atoms, and 0 to 10 heteroatoms selected from N, O, S and Si or, together with the C atom to which they are bonded, form a cyclic hydrocarbon functional group and are derived from a fragrance ketone of formula Ra-C(O)-Rb; $R_1$, $R_2$, $R_3$, $R_4$, $R_5$ and $R_6$ are each selected, independently of one another, from the group consisting of hydrogen, —ORx, —NRxRy, halogen, substituted or unsubstituted, linear or branched alkyl, alkenyl or alkinyl having up to 20, preferably up to 12, carbon atoms, substituted or unsubstituted, linear or branched heteroalkyl, heteroalkenyl or heteroalkinyl having up to 20, preferably up to 12, carbon atoms, and 1 to 6, preferably 1 to 4, heteroatoms selected from O, S and N, substituted or unsubstituted aryl having up to 20, preferably up to 12, carbon atoms, substituted or unsubstituted heteroaryl having up to 20, preferably up to 12, carbon atoms, and 1 to 6, preferably 1 to 4, heteroatoms selected from O, S and N, cycloalkyl or cycloalkenyl having up to 20, preferably up to 12, carbon atoms, and heterocycloalkyl or heterocycloalkenyl having up to 20, preferably up to 12, carbon atoms, and 1 to 6, preferably 1 to 4, heteroatoms selected from O, S and N, or in each case two of $R_1$, $R_2$, $R_3$, $R_4$, $R_5$ and $R_6$ can be combined with one another in order to form a cyclic group selected from substituted or unsubstituted aryl having up to 20, preferably up to 12, carbon atoms, substituted or unsubstituted heteroaryl having up to 20, preferably up to 12, carbon atoms, and 1 to 6, preferably 1 to 4, heteroatoms selected from O, S and N, substituted or unsubstituted cycloalkyl or cycloalkenyl having up to 20, preferably up to 12, carbon atoms, and substituted or unsubstituted heterocycloalkyl or heterocycloalkenyl having up to 20, preferably up to 12, carbon atoms, and 1 to 6, preferably 1 to 4, heteroatoms selected from O, S and N, wherein at least one of $R_1$, $R_2$, $R_3$, $R_4$, $R_5$ and $R_6$ is a functional group of formula —ORx or contains a functional group of this formula as a substituent; Rx and Ry are selected from H, substituted or unsubstituted, linear or branched alkyl, alkenyl or alkinyl having up to 20, preferably up to 12, carbon atoms, substituted or unsubstituted, linear or branched heteroalkyl, heteroalkenyl or heteroalkinyl having up to 20, preferably up to 12, carbon atoms, and 1 to 6, preferably 1 to 4, heteroatoms selected from O, S and N, substituted or unsubstituted aryl having up to 20, preferably up to 12, carbon atoms, substituted or unsubstituted heteroaryl having up to 20, preferably up to 12, carbon atoms, and 1 to 6, preferably 1 to 4, heteroatoms selected from O, S and N, cycloalkyl or cycloalkenyl having up to 20, preferably up to 12, carbon atoms, and heterocycloalkyl or heterocycloalkenyl having up to 20, preferably up to 12, carbon atoms, and 1 to 6, preferably 1 to 4, heteroatoms selected from O, S and N; and n is 0, 1, 2 or 3.

In another aspect, the present invention relates to a washing or cleaning agent containing at least one compound of formula (I) as described herein.

A further subject of the invention is a cosmetic agent that comprises at least one of the compounds of formula (I) described herein.

Yet a further subject of the invention is an air care agent containing at least one of the compounds of formula (I) according to the invention.

Yet a further subject of the invention is an insect repellent containing at least one of the compounds of formula (I) according to the invention.

Lastly, the present invention is further directed to a method for the long-lasting fragrancing of surfaces, in which a compound as described herein is applied to the surface to be fragranced, and this surface is subsequently exposed to conditions which lead to the fragrance being released.

"At least one," as used herein, refers to 1 or more, for example 2, 3, 4, 5, 6, 7, 8, 9 or more. In connection with components of the compound described herein, this statement refers not to the absolute quantity of molecules, but rather to the type of component. "At least one compound of formula (I)" therefore means, for example, one or more different compounds of formula (I), i.e. one or more different types of compounds of formula (I). Together with stated quantities, the stated quantities refer to the total quantity of the correspondingly designated type of component, as defined above.

The cyclic ketals according to the invention are compounds of formula (I).

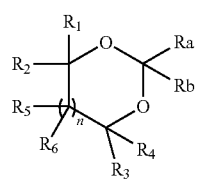

In this formula, Ra and Rb, together with the C atom to which they are bonded, are a linear, branched or cyclic, substituted or unsubstituted hydrocarbon functional group having 6 to 30, preferably 6 to 20, carbon atoms, and 0 to 10 heteroatoms selected from N, O, S and Si. In various embodiments, Ra, Rb and the C atom to which they are bonded are a functional group selected from substituted or unsubstituted, linear or branched alkyl, alkenyl or alkinyl having up to 20, preferably up to 12, carbon atoms, substituted or unsubstituted, linear or branched heteroalkyl, heteroalkenyl or heteroalkinyl having up to 20, preferably up to 12, carbon atoms, and 1 to 6, preferably 1 to 4, heteroatoms selected from O, S and N, substituted or unsubstituted aryl having up to 20, preferably up to 12, carbon atoms, substituted or unsubstituted heteroaryl having up to 20, preferably up to 12, carbon atoms, and 1 to 6, preferably 1 to 4, heteroatoms selected from O, S and N, cycloalkyl or cycloalkenyl having up to 20, preferably up to 12, carbon atoms, and heterocycloalkyl or heterocycloalkenyl having up to 20, preferably up to 12, carbon atoms, and 1 to 6, preferably 1 to 4, heteroatoms selected from O, S and N. Finally, Ra and Rb can also be combined to form a cyclic group together with the carbon atom to which they are bonded. This cyclic group can then be, depending on the specific functional group, an aryl, heteroaryl, cycloalkyl, cycloalkenyl, heterocycloalkyl or heterocycloalkenyl group selected in particular from substituted or unsubstituted aryl having up to 20, preferably up to 12, carbon atoms, substituted or unsubstituted heteroaryl having up to 20, preferably up to 12, carbon atoms, and 1 to 6, preferably 1 to 4, heteroatoms selected from O, S and N, substituted or unsubstituted cycloalkyl or cycloalkenyl having up to 20, preferably up to 12, carbon atoms, and substituted or unsubstituted heterocycloalkyl or heterocycloalkenyl having up to 20, preferably up to 12, carbon atoms, and 1 to 6, preferably 1 to 4, heteroatoms selected from O, S and N. For the selection of functional groups Ra and Rb, there is the proviso that they are selected such that they are derived from a fragrance ketone of formula Ra—C(O)-Rb. This fragrance ketone can be released again by hydrolysis of the ketal. If the fragrance ketone is, for example, an aliphatic ketone, such as undecan-2-one, this means for the compound of formula (I) that Ra is methyl and Rb is n-nonyl, or vice versa. If the fragrance ketone is, for example, acetophenone, this means for the compound of formula (I) that Ra is methyl and Rb is phenyl, or vice versa. If the fragrance ketone is, for example, menthone, Ra and Rb form together a functional group of formula —CH$_2$—CH(CH$_3$)—CH$_2$—CH$_2$—CH(CH(CH$_3$)$_2$)—.

In the compounds of formula (I), $R_1$, $R_2$, $R_3$, $R_4$, $R_5$ and $R_6$ are each selected, independently of one another, from the group consisting of hydrogen, —ORx, —NRxRy, halogen, substituted or unsubstituted, linear or branched alkyl, alkenyl or alkinyl having up to 20, preferably up to 12, carbon atoms, substituted or unsubstituted, linear or branched heteroalkyl, heteroalkenyl, or heteroalkinyl having up to 20, preferably up to 12, carbon atoms, and 1 to 6, preferably 1 to 4, heteroatoms selected from O, S and N, substituted or unsubstituted aryl having up to 20, preferably up to 12, carbon atoms, substituted or unsubstituted heteroaryl having up to 20, preferably up to 12, carbon atoms, and 1 to 6, preferably 1 to 4, heteroatoms selected from O, S and N, cycloalkyl or cycloalkenyl having up to 20, preferably up to 12, carbon atoms, and heterocycloalkyl or heterocycloalkenyl having up to 20, preferably up to 12, carbon atoms, and 1 to 6, preferably 1 to 4, heteroatoms selected from O, S and N. It is also possible, however, that in each case two of $R^1$, $R^2$, $R^3$, $R^4$, $R^5$ and $R^6$ are combined with one another to form a cyclic group together with the carbon atoms to which they are bonded. This cyclic group can then be, depending on the specific functional group, an aryl, heteroaryl, cycloalkyl, cycloalkenyl, heterocycloalkyl or heterocycloalkenyl group having the above-cited number of carbon atoms and optionally heteroatoms. In embodiments of this kind in which functional groups are combined in order to form a cyclic group, the respective functional groups can also together be a bond or a heteroatom, such as O, S or NRy. In the compounds of formula (I) according to the invention, the part of the cyclic ketal which carries the functional groups $R_1$, $R_2$, $R_3$, $R_4$, $R_5$ and $R_6$ is preferably derived from a polyol or saccharide having at least 3, preferably at least 4, 5 or 6, hydroxyl groups. Therefore, it is a proviso of the invention that at least one of $R_1$, $R_2$, $R_3$, $R_4$, $R_5$ and $R_6$ is a functional group of formula —ORx or contains a functional group of this formula as a substituent, or that two of $R_1$, $R_2$, $R_3$, $R_4$, $R_5$ and $R_6$ together form a functional group of formula —O—.

Rx and Ry are selected from H, substituted or unsubstituted, linear or branched alkyl, alkenyl, or alkinyl having up to 20, preferably up to 12, carbon atoms, substituted or unsubstituted, linear or branched heteroalkyl, heteroalkenyl or heteroalkinyl having up to 20, preferably up to 12, carbon atoms, and 1 to 6, preferably 1 to 4, heteroatoms selected from O, S and N, substituted or unsubstituted aryl having up to 20, preferably up to 12, carbon atoms, substituted or unsubstituted heteroaryl having up to 20, preferably up to 12, carbon atoms, and 1 to 6, preferably 1 to 4, heteroatoms selected from O, S and N, cycloalkyl or cycloalkenyl having up to 20, preferably up to 12, carbon atoms, and heterocycloalkyl or heterocycloalkenyl having up to 20, preferably up to 12, carbon atoms, and 1 to 6, preferably 1 to 4, heteroatoms selected from O, S and N. They are preferably H, however. In various embodiments in which two of $R_1$, $R_2$, $R_3$, $R_4$, $R_5$ and $R_6$ are combined with one another to form a cyclic group together with the carbon atoms to which they are bonded, Rx may also be omitted from the group —ORx or —NRxRy such that there is a functional group of formula —O— or —NRy- which connects the two carbon atoms.

n is 0, 1, 2 or 3, preferably 0 or 1.

In a preferred embodiment, compounds in which n equals 0 and Ra and Rb are both phenyl and/or n equals 0 and Ra or Rb is methyl and the other functional group that is not selected from Ra or Rb is pentyl are not claimed.

The ketal is preferably formed by means of vicinal or gamma-permanent hydroxyl groups of the polyol or saccharide which forms the main part of the ketal together with the keto group of the fragrance ketone. This results in 5-membered or 6-membered rings, i.e. 1,3-dioxolane or 1,3-dioxane rings in which the functional group of the fragrance ketone is attached to the C2 atom.

"Alkyl," as used herein, refers to a saturated aliphatic hydrocarbon, including straight-chain and branched-chain groups. The alkyl group preferably has 1 to 10 carbon atoms (when a numerical range "1 to 10," for example, is stated herein, this means that this group, in the present case the alkyl group, can have 1 carbon atom, 2 carbon atoms, 3 carbon atoms, etc., up to and including 10 carbon atoms). In particular, the alkyl may be a medium alkyl, having 1 to 6 carbon atoms, or a low alkyl, having 1 to 4 carbon atoms, e.g. methyl, ethyl, n-propyl, isopropyl, butyl, iso-butyl, tert-butyl, etc.

"Alkenyl" refers to an alkyl group, as defined herein, consisting of at least two carbon atoms and at least one carbon-carbon double bond, e.g. ethenyl, propenyl, butenyl or pentenyl and the structural isomers thereof such as 1-propenyl or 2-propenyl, 1-butenyl, 2-butenyl or 3-butenyl, etc.

"Alkinyl" refers to an alkyl group, as defined herein, consisting of at least two carbon atoms and at least one carbon-carbon triple bond, e.g. ethinyl (acetylene), propinyl, butinyl or pentinyl and the structural isomers thereof as described above.

"Heteroalkyl," "heteroalkenyl" and "heteroalkinyl," as used herein, refer to alkyl, alkenyl, and alkinyl groups, respectively, as defined above, in which one or more carbon atoms are replaced by heteroatoms, in particular selected from O, S, N and Si, e.g. ethoxyethyl, ethoxyethenyl, isopentoxypropyl and alkoxy functional groups of formula —O-alkyl, e.g. methoxy, ethoxy, propoxy, etc. In functional groups of this kind, it is preferable for no two heteroatoms to be directly bonded to one another, i.e. no structural units of formula —O—O— or similar to be contained.

A "cycloalkyl" group refers to monocyclic or polycyclic (multiple rings having shared carbon atoms) groups consisting in particular of 3 to 8 carbon atoms, in which the ring does not have any double bonds, i.e. acyclic saturated groups, e.g. cyclopropyl, cyclobutyl, cyclopentyl, cyclohexyl, etc. Examples of cycloalkyl groups are cyclopropane, cyclobutane, cyclopentane, cyclohexane, adamantane and cycloheptane. Accordingly, "cycloalkenyl" refers to corresponding cyclic groups which have at least one double bond but do not have a complete conjugated pi electron system, i.e. are not aromatics. Examples of functional groups of this kind are cyclobutenyl, cyclopentenyl, cyclohexenyl, etc. Cycloalkenyl groups include, but are not limited to, cyclopentene, cyclohexene, cyclohexadiene and cycloheptatriene.

"Aryl" refers to monocyclic or polycyclic (i.e. rings having shared neighboring carbon atom pairs) groups consisting in particular of 6 to 14 carbon ring atoms that have a complete conjugated pi electron system. Examples of aryl groups are phenyl, naphthalenyl, and anthracenyl.

A "heteroaryl" group refers to a monocyclic or polycyclic (i.e. rings that share a neighboring ring atom pair) aromatic ring consisting in particular of 5 to 10 ring atoms, one, two, three or four ring atoms being nitrogen, oxygen or sulfur and the remainder carbon. Examples of heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, pthalazinyl, quinoxalinyl, cinnolinyl, naphthyridinyl, quinolyl, isoquinolyl, tetrazolyl, 5,6,7,8-tetrahydroquinolyl, 5,6,7,8-tetrahydroisoquinolyl, purinyl, pteridinyl, pyridinyl, pyrimidinyl, carbazolyl, xanthenyl or benzoquinolyl.

A "heterocycloalkyl" group refers to a monocyclic or fused ring, consisting of 5 to 10 ring atoms and containing one, two or three heteroatoms selected from N, O and S, the remainder of the ring atoms being carbon. A "heterocycloalkenyl" group additionally contains one or more double bonds. However, the ring does not have a complete conjugated pi electron system. Examples of heteroalicyclic groups are pyrrolidine, piperidine, piperazine, morpholine, imidazolidine, tetrahydropyridazine, tetrahydrofuran, thiomorpholine, tetrahydropyridine and the like.

"Substituted," as used herein in connection with the substituents and functional groups according to the invention, means that one or more H atoms are replaced by other functional groups in the group in question, these functional groups being selected in particular from those containing one or more heteroatoms. In various embodiments, the substituents are selected from =O, =S, —OH, —SH, —NH$_2$—NO$_2$, —CN, —F, —Cl, —Br, $C_{1-10}$ alkyl, $C_{2-10}$ alkenyl, $C_{2-10}$ alkinyl, $C_{3-8}$ cycloalkyl, $C_{6-14}$ aryl, a 5 to 10-membered heteroaryl ring in which 1 to 4 ring atoms are independently nitrogen, oxygen or sulfur, and a 5 to 10-membered heteroalicyclic ring in which 1 to 3 ring atoms are independently nitrogen, oxygen or sulfur.

In various embodiments of the present invention, the compounds according to the invention are those of formula (II):

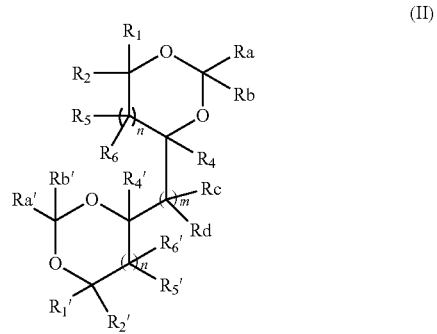

(II)

In this formula, Ra, Rb, $R_1$, $R_2$, $R_4$, $R_5$, $R_6$ and n are defined as above. Furthermore, Ra', Rb', $R_1'$, $R_2'$, $R_4'$, $R_5'$ and $R_6'$ have the same definition as Ra, Rb, $R_1$, $R_2$, $R_4$, $R_5$ and $R_6$, respectively, but are selected independently thereof. Rc and Rd are independently selected from hydrogen, —ORx, —NRxRy, halogen, substituted or unsubstituted, linear or branched alkyl, alkenyl, or alkinyl having up to 20, preferably up to 12, carbon atoms, substituted or unsubstituted, linear or branched heteroalkyl, heteroalkenyl or heteroalkinyl having up to 20, preferably up to 12, carbon atoms, and 1 to 6, preferably 1 to 4, heteroatoms selected from O, S and N, substituted or unsubstituted aryl having up to 20, preferably up to 12, carbon atoms, substituted or unsubstituted heteroaryl having up to 20, preferably up to 12, carbon atoms, and 1 to 6, preferably 1 to 4, heteroatoms selected from O, S and N, cycloalkyl or cycloalkenyl having up to 20, preferably up to 12, carbon atoms, and heterocycloalkyl or heterocycloalkenyl having up to 20, preferably up to 12, carbon atoms, and 1 to 6, preferably 1 to 4, heteroatoms selected from O, S and N, Rx and Ry being defined as above. It is possible, however, that one of Rc and Rd is combined with one of $R^1$, $R^2$, $R^3$, $R^4$, $R^5$, $R^6$, $R_1'$, $R_2'$, $R_3'$, $R_4'$, $R_5'$ and $R_6'$ in order to form a cyclic group together with the carbon atoms to which they are bonded. This cyclic group can then be, depending on the specific functional group, an aryl, heteroaryl, cycloalkyl, cycloalkenyl, heterocycloalkyl or heterocycloalkenyl group. In embodiments of this kind in which functional groups are combined in order to form a cyclic group, the respective functional groups can also together be a bond or a heteroatom, such as O, S or NRy. It is preferable for either Rc or Rd to be a group of formula —ORx where Rx=H, or to form a group of formula —O— together with one of the functional groups $R^1$, $R^2$, $R^3$, $R^4$, $R^5$, $R^6$, $R_1'$, $R_2'$, $R_3'$, $R_4'$, $R_5'$ and $R_6'$. m is 0 or an integer from 1 to 10, preferably 0, 1, 2 or 3, particularly preferably 1 or 2, most preferably 2.

In various embodiments of the compounds of formula (II), the total of all instances of n and m is 1, 2, 3 or 4, preferably 2. This means that, for example, both instances of n equal 0 and m equals 2, or one instance of n equals 1, one instance of n equals 0 and m equals 1.

In the compounds of formula (II) according to the invention, the part of the cyclic ketal which carries the functional groups $R^1$, $R^2$, $R^3$, $R^4$, $R^5$, $R^6$, $R_1'$, $R_2'$, $R_3'$, $R_4'$, $R_5'$ and $R_6'$ is preferably derived from a polyol or saccharide having at least 3, preferably at least 4, 5 or 6, hydroxyl groups such as mannitol or L-sorbose.

Generally, the polyols or saccharides that form the backbone of the ketal can preferably be selected from sugar alcohols and monosaccharides, including, but not limited to, glycerol, mannitol, isomaltol, lactitol, sorbitol (or glucitol) and xylitol, threitol, erythritol, arabitol, erythrose, threose, ribose, arabinose, xylose, lyxose, allose, altrose, glucose, mannose, gulose, idose, galactose, talose, erythrulose, ribulose, xylulose, psicose, fructose, sorbose and tagatose. The simple sugars can be used in D or L form, but typically in their D form.

In various preferred embodiments, in the compounds of formula (I) $R_1$, $R_2$ and $R_4$ are hydrogen. $R^3$ is preferably a substituted alkyl or heteroalkyl functional group having 2 to 6 carbon atoms, preferably 2 to 4 carbon atoms, and optionally one or more oxygen atoms. The alkyl functional group in this embodiment is preferably substituted with one or more hydroxyl groups. In particular, in embodiments of this kind, $R_3$ can be a functional group having a second cyclic ketal group, for example of formula —(CRcRd)$_m$- (cyclic ketal). In embodiments of this kind, the result is a compound of formula (II). If n equals 1 or more, $R_5$ is then preferably H and $R_6$ is preferably not hydrogen, but rather preferably —OH.

In the compounds of formula (II), $R_1$, $R_2$, $R_4$, $R_1'$, $R_2'$ and $R_4'$ are hydrogen in various embodiments. All instances of n preferably equal 0 or 1, particularly preferably 0. If one instance of n equals 1 or more, $R_5$ or $R_5'$ is then preferably H and $R_6$ or $R_6'$ is preferably not hydrogen, but rather preferably —OH, or forms, together with $R_4$ or $R_4'$ ($R_6$ together with $R_4'$ or $R_6'$ together with $R_4$), a group of formula —O—. In embodiments of this kind, m is preferably 1 or 2. Rc is then preferably H and Rd is preferably —OH. In embodiments of this kind, the sum of all instances of n and m is preferably 2.

Particularly preferred compounds of formula (II) are those of formulas (III) and (IV):

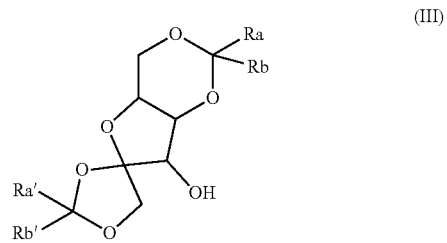

(III)

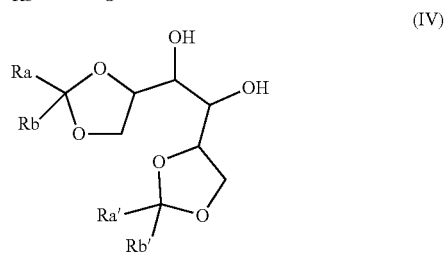

(IV)

In this formula, Ra, Rb, Ra' and Rb' are defined as above and are in particular functional groups which are derived from a fragrance ketone of formula Ra—C(O)-Rb or Ra'-C(O)-Rb'. "Derived functional group," as used in this connection, refers to functional groups Ra/Rb and Ra'/Rb' which are derived from fragrance ketones in that the carbon atom in the C2 position of the cyclic ketal is the carbon atom that carries the oxygen atom in the fragrance ketone, i.e. that forms the keto group. When the fragrance is released, for example by enzymatic or chemical hydrolysis, the ketal is cleaved such that the fragrance ketone and the corresponding polyol are produced as cleavage products.

DETAILED DESCRIPTION OF THE INVENTION

The compounds of formulas (I)-(IV) according to the invention are suitable as a pro-fragrance for all fragrance ketones that are known in the prior art and suited for this purpose. "Fragrance ketone," as used herein, refers to odorants of natural or synthetic origin which contain at least one keto group.

In various embodiments, the fragrance ketones which are bonded in the cyclic ketal structure according to formulas (I)-(IV) and which can be released by hydrolysis are selected from the group consisting of Buccoxime; isojasmone; methyl beta-naphthyl ketone; musk indanone; tonalide/Musk Plus; alpha-damascone, beta-damascone, delta-damascone, gamma-damascone, damascenone, damask rose, methyl dihydrojasmonate (hedione), menthone, carvone, camphor, fenchone, alpha-ionone, beta-ionone, gamma-methylionone, fleuramone, dihydrojasmone, cis-jasmone, Iso E Super (1-(1,2,3,4,5,6,7,8-octahydro-2,3,8,8,-tetramethyl-2-naphthyl)ethan-1-one), methyl cedrenyl ketone, methyl cedrylone, acetophenone, methylacetophenone, para-methoxyacetophenone, methyl beta-naphthyl ketone, benzylacetone, benzophenone, para-hydroxyphenylbutanone, celery ketone or livescone, 6-isopropyldecahydro-2-naphtone, dimethyl octenone, frescomenthe, 4-(1-ethoxyvinyl)-3,3,5,5-tetramethylcyclohexanone, methyl heptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H) indanone, 4-damascol (5-methyl-5-phenyl-3-hexanone), dulcinyl, cassione, gelsone, hexalone, Isocyclemone E, methyl cyclocitrone, methyl lavender ketone, orivone, para-tertiary butylcyclohexanone, verdone, delphone, muscone, neobutenone, plicatone, veloutone, 2,4,4,7-tetramethyl-oct-6-en-3-one and tetramerane.

They are particularly preferably selected from the group consisting of Buccoxime; isojasmone; methyl beta-naphthyl ketone; musk indanone; tonalide/Musk Plus; alpha-damascone, beta-damascone, delta-damascone, gamma-damascone, damascenone, damask rose, methyl dihydrojasmonate (hedione), menthone, carvone, camphor, fenchone, alpha-ionone, beta-ionone, gamma-methylionone, fleuramone, dihydrojasmone, cis-jasmone, Iso E Super (1-(1,2,3,4,5,6,7,8-octahydro-2,3,8,8,-tetramethyl-2-naphthyl)ethan-1-one), methyl cedrenyl ketone, methyl cedrylone, acetophenone, methylacetophenone, para-methoxyacetophenone, methyl beta-naphthyl ketone, benzylacetone, para-hydroxyphenylbutanone, celery ketone or livescone, 6-isopropyldecahydro-2-naphtone, dimethyl octenone, frescomenthe, 4-(1-ethoxyvinyl)-3,3,5,5-tetramethylcyclohexanone, methyl heptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbomane, 6,7-dihydro-1,1,2,3,3-pentamethyl-4(5H) indanone, 4-damascol (5-methyl-5-phenyl-3-hexanone), dulcinyl, cassione, gelsone, hexalone. Isocyclemone E, methyl cyclocitrone, methyl lavender ketone, orivone, para-tertiary butylcyclohexanone, verdone, delphone, muscone, neobutenone, plicatone, veloutone, 2,4,4,7-tetramethyl-oct-6-en-3-one and tetramerane.

In a preferred embodiment, diphenylmethanone and pinacolone are not claimed.

In general, the following are also suitable fragrance ketones, without the invention being limited thereto: 4-methoxyphenyl-ethanone; 1-[6-(1,1-dimethylethyl)-2,3-dihydro-1,1-dimethyl-1H-inden-4-yl]ethanone; 1-(5,6,7,8-tetrahydro-3,5,5,6,8,8-hexamethyl-2-naphthalinyl)ethanone; 2-(1-methylethyl)-indanone; 4-tert-butyl-3,5-dinitro-2,6-dimethyl-acetophenone; 1,6,7,8-tetrahydro-1,4,6,6,8,8-hexamethyl-as-indacen-3(2H)-one; 1-(2-dapthalenyl) ethanone; 1-(2,3-dihydro-1,1,2,3,3,6-hexamethyl-1H-inden-5-yl)ethanone; 1-[2,3-dihydro-1,1,2,6-tetramethyl-3-(1-methylethyl)-1H-inden-5-yl]ethanone; 3-methyl-1-(4-methylphenyl)-4-hexen-1-one; 5-acetyl-1,1,2,3,3-pentamethylindane; 1-phenylpropanone; acetophenone; 2,4-dimethylphenyl-ethanone; 1-[4-(1,1-dimethylethyl)-2,6-dimethylphenyl]ethanone; 1-(hexahydrodimethyl-1H-benzindenyl)ethanone; 1-(5,6,7,8-tetrahydro-2-naphthalinyl)ethanone; 1-phenyl-4-penten-1-one; 1-(5,6,7,8-tetrahydro-3,5,5,8,8-pentamethyl-2-naphthalinyl) ethanone; 1-(3-ethyl-5,6,7,8-tetrahydro-5,5,8,8-tetramethyl-2-naphthalinyl)ethanone; 2,5-dimethyl-oct-2-en-6-one; 4-(2,6,6-trimethylcyclohex-1-en-1-yl)-butan-2-one; 4-(2,6,6-trimethylcyclohex-2-en-1-yl)-butan-2-one; 2-methyl-5-(1-methylethenyl)-cyclohex-2-en-1-one; 1-(4-hydroxyphenyl)-butan-3-one; 4-benzo-1,3-dioxo-5-yl-but-2-one; 2-heptyl-cyclopentanon-nonan-2-one; octan-2-one; 2,2,6,10-tetrametyltricyclo-[5.4.0.0(6,10)]-undecan-4-one; heptan-2-one; undecan-2-one; decan-2-one; benzylacetone; butan-2-one; 1,2,3,5,6,7-hexahydro-1,1,2,3,3 pentamethyl-4H-inden-4-one; 6-methyl-hept-5-en-2-one; 2-(butan-2-yl)-cyclohexanone; 2-hexyl-cyclopent-2-en-1-one; 2-(1-methylethyl)-5-methyl-cyclohexanone; 2-(2-methylethyl)-5-methyl-cyclohexanone; 3-methyl-cyclopentadecanone; 4-(1,1-dimethylpropyl)-cyclohexanone; 6,10-dimethyl-undeca-5,9-dien-2-one; 3-oxo-2-pentyl-cyclopentan-acetic acid-methyl ester; 1-(1,2,3,4,5,6,7,8-octahydro-2,3,8,8-tetramethyl-2-naphthalinyl)ethanone; 3-methyl-5-propyl-cyclohex-2-en-1-one; 1-(2-cyclohexen)-2,4,4-trimethyl-but-2-enone; carvone; 2-hexyl-cyclo-pent-2-en-1-one; 2-pentyl-cyclopent-2-en-1-one; 3-methyl-2-pentyl-cyclopent-2-en-1-one; 2-hexyliden-cyclopentanone; 3,5-diethyl-5,6-dimethyl-2-cyclohexenone; 4,4a,5,6,7,8-hexahydro-6-isopropenyl-4,4a-dimethyl-2(3H)-napthalenone; 3-methyl-6-propylidenecyclohexanone; 4-(1-methylethyl)-cyclohex-2-en-1-one; (E)-oct-3-en-2-one; 1-(2,3,4,7,8,8A-hexahydro-3,6,8,8-tetramethyl-1H-3a,7-methanoazulen-5-yl)-ethanone; 2-hydroxy-3,5-dimethyl-cyclopent-2-en-1-one; 1-(3,3-dimethyl-1-cyclohexen-1-yl)ethanone; 1-(2,4,6-trimethylcyclohex-3-en-1-yl)-but-1-en-3-one; acetyl isolongifolene; 2-(3-methylbut-2-en-1-yl)-3-methyl-cyclopent-2-en-1-one; 3-methyl-5-(2,2,3-trimethyl cyclopent-3-en-1-yl)pent-3-en-2-one; 5-butyliden-2,2,4-trimethylcyclopentanone; 1,2,3,5,6,7-hexahydro-1,1,2,3,3-pentamethyl-4H-inden-4-one; 3-methyl-5-propyl-cyclohex-2-en-1-one; 4,4a,5,6,7,8-hexahydro-6-isopropyl-2(3H)-naphthalinone; 3,5,5-trimethyl-cyclohex-2-en-1,4-dione; (E)-5-methyl-2-hepten-4-one; acetyl diisoamylene; dec-3-en-2-one; 2-ethyl-3,6,6-trimethylcyclohex-2-enyl-but-2-en-1-one; 1-(5,5-dimethyl-1(6)-cyclohexen-1-yl)-4-penten-1-one; 1-(2,6,6-trimethyl-1-cyclohexen-1-yl)but-2-en-1-one; 1-(2,6,6-trimethyl-2-cyclohexen-1-yl)but-2-en-1-one; 1-(2,6,6-trimethyl-3-cyclohexen-1-yl)but-2-en-1-one; 2,4,4,5,5-pentamethyl-1-cyclopenten-1-yl-ethanone.

In various embodiments of the invention, the compounds of formulas (I) to (IV) are therefore compounds in which Ra/Rb and/or Ra'/Rb' are selected such that they correspond to the functional groups of the above-mentioned fragrance ketones that flank the keto group. If, for example, undecan-2-one is used as a fragrance ketone, in the compounds of formulas (III) and (IV), Ra and Ra' are methyl and Rb and Rb' are n-nonyl. If, for example, menthone is used as a fragrance, Ra and Rb and Ra' and Rb', respectively, are together the functional group —$CH_2$—$CH(CH_3)$—$CH_2$—$CH_2$—$CH(CH(CH_3)_2)$—. The above-mentioned specific compounds are embodiments of the invention.

The compounds according to the invention can be stably incorporated into typical washing or cleaning agent matrices, cosmetics and existing odorant compositions. They provide for a delayed release of the stored fragrance ketones. Preferred fragrances are, for example, damascones. These fragrances impart a particularly long-lasting impression of freshness to typical washing or cleaning agents and cosmetics. In particular the dried, washed textile benefits from the good fragrance effect of long-term freshness. The stored odorant is released slowly by hydrolysis of the compounds, which can be achieved using enzymes or by means of an acidic or basic medium.

A further subject of the present invention is a washing or cleaning agent, preferably a washing agent, softener or auxiliary washing agent, containing at least one compound of formula (I), said compound preferably being contained in amounts of between 0.0001 and 5 wt. %, advantageously between 0.001 and 4 wt. %, more advantageously between 0.005 and 3 wt. %, in particular between 0.01 and 2 wt. %, in each case based on the total weight of the agent. Suitable cleaning agents are, for example, cleaning agents for hard surfaces, in particular dishwasher detergents. The cleaning agent may also be, for example, a household cleaner, all-purpose cleaner, window cleaner, floor cleaner, etc. In various embodiments, the cleaning agent may be a product for cleaning toilet bowls and urinals, in particular a flush cleaner for being hung in the toilet bowl.

According to a preferred embodiment of the invention, the washing or cleaning agent according to the invention contains at least one surfactant selected from anionic, cationic, nonionic, zwitterionic and amphoteric surfactants or mixtures thereof.

According to a further preferred embodiment of the invention, the agent according to the invention is present in solid or liquid form.

A further subject of the invention is a cosmetic agent containing at least one compound according to formula (I), which agent preferably contains the compound in amounts of between 0.0001 and 50 wt. %, advantageously between 0.001 and 5 wt. %, more advantageously between 0.005 and 3 wt. %, in particular between 0.01 and 2 wt. %, in each case based on the overall agent.

A further subject of the invention is an air care agent (e.g. air freshener, room deodorizer, room spray, etc.) containing at least one compound according to formula (I), the compound of formula (I) preferably being contained in amounts of between 0.0001 and 50 wt. %, preferably between 0.001 and 5 wt. %, more preferably between 0.01 and 3 wt. %, particularly preferably between 0.1 and 2 wt. %, in each case based on the total weight of the agent.

A further subject of the invention is an insect repellent (e.g. insect spray, scented room spray, mosquito net, insect traps, etc.) containing at least one compound according to formula (I), the compound of formula (I) preferably being contained in amounts of between 0.0001 and 50 wt. %, preferably between 0.001 and 5 wt. %, more preferably between 0.01 and 3 wt. %, particularly preferably between 0.1 and 2 wt. %, in each case based on the total weight of the agent.

According to a further preferred embodiment of the invention, additional fragrances are contained in an agent according to the invention (i.e. a washing or cleaning agent, cosmetic agent, air care agent or insect repellent), which additional fragrances are in particular selected from the group comprising fragrances of natural or synthetic origin, preferably more volatile fragrances, higher-boiling fragrances, solid fragrances and/or semisolid fragrances.

Examples of semisolid odorants that are advantageously usable within the scope of the present invention are essential oils such as angelica root oil, anise oil, arnica blossom oil, basil oil, bay oil, bergamot oil, champaca blossom oil, abies alba oil, abies alba cone oil, elemi oil, eucalyptus oil, fennel oil, spruce needle oil, galbanum oil, geranium oil, ginger grass oil, guaiac wood oil, gurjun balsam oil, helichrysum oil, ho oil, ginger oil, iris oil, cajeput oil, calamus oil, chamomile oil, camphor oil, cananga oil, cardamom oil, cassia oil, pine needle oil, copaiba balsam oil, coriander oil, spearmint oil, caraway oil, cumin oil, lavender oil, lemon grass oil, lime oil, mandarin oil, melissa oil, musk seed oil, myrrh oil, clove oil, neroli oil, niaouli oil, olibanum oil, orange oil, oregano oil, palmarosa oil, patchouli oil, Peru balsam oil, petitgrain oil, pepper oil, peppermint oil, allspice oil, pine oil, rose oil, rosemary oil, sandalwood oil, celery oil, spike lavender oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, lemon oil and cypress oil.

However, higher-boiling and solid odorants of natural or synthetic origin can also be used within the scope of the present invention as semisolid odorants or odorant mixtures, i.e. fragrances. These compounds include the compounds indicated in the following and mixtures thereof: Ambretolide, alpha-amylcinnamaldehyde, anethole, anisaldehyde, anise alcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerianate, borneol, bornyl acetate, alpha-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl n-amyl ketone, methylanthranilic acid methyl ester, p-methylacetophenone, methylchavicol, p-methylquinoline, methyl beta-naphthyl ketone, methyl n-nonyl acetaldehyde, methyl-n-nonyl ketone, muscone, beta-naphthol ethyl ether, beta-naphthol methyl ether, nerol, nitrobenzene, n-nonyl aldehyde, nonyl alcohol, n-octylaldehyde, p-oxyacetophenone, pentadecanolide, beta-phenylethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, gamma-undecalactone, vanillin, veratraldehyde, cinnamaldehyde, cinnamyl alcohol, cinnamic acid, cinnamic acid ethyl ester and cinnamic acid benzyl ester. More volatile fragrances include in particular lower-boiling odorants of natural or synthetic origin, which can be used alone or in mixtures. Examples of more volatile fragrances are alkyl isothiocyanates (alkyl mustard oils), butanedione, limonene, linalool, linalyl acetate and propionate, menthol, menthone, methyl-n-heptenone, phellandrene, phenylacetaldehyde, terpinyl acetate, citral and citronellal.

According to a further preferred embodiment, the agent according to the invention (i.e. a washing or cleaning agent, cosmetic agent, air care agent or insect repellent) comprises at least one, preferably a plurality of, active components, in particular components that have a washing, caring and/or cleaning effect and/or are cosmetic, advantageously selected from the group comprising anionic surfactants, cationic surfactants, amphoteric surfactants, nonionic surfactants, acidifying agents, alkalizing agents, anti-crease compounds, antibacterial substances, antioxidants, anti-redeposition agents, antistatic agents, builders, bleaching agents, bleach activators, bleach stabilizers, bleach catalysts, ironing aids, cobuilders, fragrances, anti-shrink agents, electrolytes, enzymes, color protectants, colorants, dyes, dye transfer inhibitors, fluorescing agents, fungicides, germicides, odor-complexing substances, adjuvants, hydrotropes, rinse aids, complexing agents, preservatives, corrosion inhibitors, water-miscible organic solvents, optical brighteners, perfumes, perfume carriers, luster agents, pH adjusters, repellents and impregnating agents, polymers, anti-swelling and anti-slip agents, foam inhibitors, phyllosilicates, soil-repellent substances, silver protectants, silicone oils, soil-release active ingredients, UV protection substances, viscosity regulators, thickeners, discoloration inhibitors, graying inhibitors, vitamins and/or softeners. Within the meaning of the present invention, unless indicated otherwise, stated amounts in wt. % refer to the total weight of the agent according to the invention.

The amounts of the individual ingredients in the agents according to the invention (i.e. washing or cleaning agents, cosmetic agents or air care agents) in each case depend on the intended purpose of the agents in question, and a person skilled in the art is in principle familiar with the ranges of the amounts of ingredients that should be used, or can obtain these from the relevant technical literature. Depending on the intended purpose of the agents according to the invention, the surfactant content, for example, is selected to be higher or lower. The surfactant content of washing agents can typically be, for example, between 10 and 50 wt. %, preferably between 12.5 and 30 wt. %, and in particular between 15 and 25 wt. %, while, for example, cleaning agents for automatic dishwashing may contain, for example, between 0.1 and 10 wt. %, preferably between 0.5 and 7.5 wt. %, and in particular between 1 and 5 wt. %, of surfactants.

The agents according to the invention (i.e. washing or cleaning agents, cosmetic agents or air care agents) can contain surfactants, preferably anionic surfactants, nonionic surfactants and mixtures thereof, but also cationic surfactants. Suitable nonionic surfactants are in particular ethoxylation and/or propoxylation products of alkyl glycosides and/or linear or branched alcohols each having 12 to 18 carbon atoms in the alkyl portion and 3 to 20, preferably 4 to 10, alkyl ether groups. Also usable are corresponding ethoxylation and/or propoxylation products of N-alkylamines, vicinal diols, fatty acid esters and fatty acid amides which, with regard to the alkyl portion, correspond to the stated long-chain alcohol derivatives, and of alkylphenols having 5 to 12 carbon atoms in the alkyl functional group.

Suitable anionic surfactants are in particular soaps and those containing sulfate or sulfonate groups preferably having alkali ions as cations. Usable soaps are preferably the alkali salts of saturated or unsaturated fatty acids having 12 to 18 carbon atoms. Fatty acids of this kind can also be used in a not completely neutralized form. Sulfate-type surfactants that can be used include the salts of sulfuric acid semiesters of fatty alcohols having 12 to 18 carbon atoms and the sulfation products of the mentioned nonionic surfactants having a low degree of ethoxylation. Sulfonate-type surfactants that can be used include linear alkylbenzenesulfonates having 9 to 14 carbon atoms in the alkyl portion, alkanesulfonates having 12 to 18 carbon atoms, and olefin sulfonates having 12 to 18 carbon atoms, resulting from the reaction of corresponding monoolefins with sulfur trioxide, and alpha-sulfo fatty acid esters, resulting from the sulfonation of fatty acid methyl or ethyl esters.

Cationic surfactants are preferably selected from among esterquats and/or quaternary ammonium compounds (QACs) according to general formula $(R^I)(R^{II})(R^{III})(R^{IV})N^+ X^-$, in which $R^I$ to $R^{IV}$ represent $C_{1-22}$ alkyl functional groups, $C_{7-28}$ arylalkyl functional groups or heterocyclic functional groups that are the same or different, where two functional groups, or, in the case of aromatic bonding such as in pyridine, even three functional groups form, together with the nitrogen atom, the heterocycle, e.g. a pyridinium or imidazolinium compound, and $X^-$ represents halide ions, sulfate ions, hydroxide ions or similar anions. QACs can be prepared by reacting tertiary amines with alkalizing agents, for example methyl chloride, benzyl chloride, dimethyl sulfate, dodecyl bromide, but also ethylene oxide. The alkylation of tertiary amines having a long alkyl functional group and two methyl groups is particularly simple; the quaternization of tertiary amines having two long functional groups and a methyl group can also be carried out under mild conditions using methyl chloride. Amines having three long alkyl functional groups or hydroxy-substituted alkyl functional groups are less reactive, and are quaternized using dimethyl sulfate, for example. Examples of suitable QACs are benzalkonium chloride (N-alkyl-N,N-dimethylbenzylammonium chloride), Benzalkon B (m,p-dichlorobenzyldimethyl-$C_{12}$ alkylammonium chloride, benzoxonium chloride (benzyldodecyl-bis-(2-hydroxyethyl) ammonium chloride), cetrimonium bromide (N-hexadecyl-N,N-trimethylammonium bromide), benzethonium chloride (N,N-dimethyl-N-[2-[2-[p-(1,1,3,3-tetramethylbutyl)phenoxy]ethoxy]ethyl]benzylammonium chloride), dialkyldimethylammonium chlorides such as di-n-decyldimethyl ammonium chloride, didecyldimethyl ammonium bromide, dioctyldimethyl ammonium chloride, 1-cetylpyridinium chloride, and thiazoline iodide, and mixtures thereof. Preferred QACs are benzalkonium chlorides having $C_8$-$C_{22}$ alkyl functional groups, in particular $C_{12}$-$C_{14}$ alkylbenzyldimethyl ammonium chloride.

Preferred esterquats are methyl-N-(2-hydroxyethyl)-N,N-di(talgacyl-oxyethyl) ammonium methosulfate, bis-(palmitoyl)-ethyl-hydroxyethyl-methyl-ammonium methosulfate or methyl-N,N-bis(acyl-oxyethyl)-N-(2-hydroxyethyl)ammonium methosulfate. Commercially available examples are the methylhydroxyalkyldialkoyloxyalkyl ammonium methosulfates marketed by Stepan under the trademark Stepantex®, the products from BASF SE known under the trade name Dehyquart, or the products from the manufacturer Evonik known under the name Rewoquat.

Surfactants are contained in the agents according to the invention (i.e. washing or cleaning agents, cosmetic agents or air care agents) in amount proportions of preferably from 5 wt. % to 50 wt. %, in particular from 8 wt. % to 30 wt. %. Preferably up to 30 wt. %, in particular from 5 wt. % to 15 wt. %, of surfactants, preferably including cationic surfactants at least in portions, are used in particular in laundry post-treatment agents.

An agent according to the invention, in particular a washing or cleaning agent, preferably contains at least one water-soluble and/or water-insoluble, organic and/or inorganic builder. The water-soluble organic builders include polycarboxylic acids, in particular citric acid and saccharic acids, monomeric and polymeric aminopolycarboxylic acids, in particular methylglycinediacetic acid, nitrilotriacetic acid, ethylenediaminetetraacetic acid and polyaspartic acid, polyphosphonic acids, in particular amino tris(methylenephosphonic acid), ethylenediamine tetrakis(methylenephosphonic acid) and 1-hydroxyethane-1,1-diphosphonic acid, polymeric hydroxy compounds such as dextrin, and polymeric (poly)carboxylic acids, polymeric acrylic acids, methacrylic acids, maleic acids, and mixed polymers thereof, which may also contain, in the polymer, small portions of polymerizable substances, without a carboxylic acid functionality. Compounds of this class which are suitable, although less preferred, are copolymers of acrylic acid or methacrylic acid with vinyl ethers, such as vinyl methyl ethers, vinyl esters, ethylene, propylene and styrene, in which the proportion of the acid is at least 50 wt. %. The organic builders may, in particular for the preparation of liquid agents, be used in the form of aqueous solutions, preferably in the form of 30 to 50 wt. % aqueous solutions. All indicated acids are generally used in the form of the water-soluble salts thereof, in particular alkali salts thereof.

Organic builders, if desired, can be contained in amounts of up to 40 wt. %, in particular up to 25 wt. %, and preferably from 1 wt. % to 8 wt. %. Amounts close to the stated upper limit are preferably used in paste-form or liquid, in particular water-containing, agents according to the invention. Laundry post-treatment agents according to the invention, such as softeners, can optionally also be free of organic builders.

In particular alkali silicates and polyphosphates, preferably sodium triphosphate, are suitable as water-soluble inorganic builder materials. In particular crystalline or amorphous alkali aluminosilicates, if desired, can be used as water-insoluble, water-dispersible inorganic builder materials in amounts of up to 50 wt. %, preferably no greater than 40 wt. %, and in liquid agents in particular in amounts of from 1 wt. % to 5 wt. %. Among these, crystalline sodium aluminosilicates of washing agent quality, in particular zeolite A, P and optionally X, are preferred. Amounts close to the stated upper limit are preferably used in solid particulate agents. Suitable aluminosilicates have in particular no particles having a particle size greater than 30 μm and preferably comprise at least 80 wt. % of particles having a size smaller than 10 μm.

Suitable substitutes or partial substitutes for the stated aluminosilicate are crystalline alkali silicates, which may be present alone or in a mixture with amorphous silicates. The alkali silicates that can be used in the agents according to the invention as builders preferably have a molar ratio of alkali oxide to $SiO_2$ of less than 0.95, in particular from 1:1.1 to 1:12, and may be present in amorphous or crystalline form. Preferred alkali silicates are sodium silicates, in particular amorphous sodium silicates having a $Na_2O:SiO_2$ molar ratio of from 1:2 to 1:2.8. Preferably used as crystalline silicates, which may be present alone or in a mixture with amorphous silicates, are crystalline phyllosilicates of general formula $Na_2Si_xO_{2x+1} \cdot y\, H_2O$, where x, referred to as the module, is a number from 1.9 to 4, y is a number from 0 to 20, and preferred values for x are 2, 3 or 4. Preferred crystalline phyllosilicates are those in which x in the stated general formula assumes the values 2 or 3. In particular, both beta-sodium and delta-sodium disilicates ($Na_2Si_2O_5 \cdot y\, H_2O$) are preferred. Practically water-free crystalline alkali silicates which have the above general formula, in which x is a number from 1.9 to 2.1, and which are prepared from amorphous alkali silicates may also be used in agents according to the invention. In a further preferred embodiment of agents according to the invention, a crystalline sodium phyllosilicate having a module of from 2 to 3, as can be prepared from sand and soda, is used. Crystalline sodium silicates having a module in the range of from 1.9 to 3.5 are used in a further preferred embodiment of agents according to the invention. If alkali aluminosilicate, in particular zeolite, is also present as an additional builder, the weight ratio of aluminosilicate to silicate, based in each case on water-free active substances, is preferably from 1:10 to 10:1. In agents containing both amorphous and crystalline alkali silicates, the weight ratio of amorphous alkali silicate to crystalline alkali silicate is preferably from 1:2 to 2:1 and in particular from 1:1 to 2:1.

Builders are, if desired, preferably contained in the agents according to the invention in amounts of up to 60 wt. %, in particular from 5 wt. % to 40 wt. %. Laundry post-treatment agents according to the invention, for example softeners, are preferably free of inorganic builders.

Suitable peroxygen compounds are, in particular, organic peracids or peracid salts of organic acids, such as phthalimidopercapronic acid, perbenzoic acid, or salts of diperdodecanedioic acid, hydrogen peroxide and inorganic salts that release hydrogen peroxide under the conditions of use, such as perborate, percarbonate and/or persilicate. If solid peroxygen compounds are intended to be used, these may be used in the form of powders or granules, which may also be coated in a manner known in principle. The optional use of alkali percarbonate, alkali perborate monohydrate or, in particular in liquid agents, hydrogen peroxide in the form of aqueous solutions containing from 3 wt. % to 10 wt. % of hydrogen peroxide is particularly preferred. If an agent according to the invention contains bleaching agents, such as preferably peroxygen compounds, these are present in amounts of preferably up to 50 wt. %, in particular from 5 wt. % to 30 wt. %. The addition of small amounts of known bleaching agent stabilizers such as phosphonates, borates or metaborates, metasilicates and magnesium salts such as magnesium sulfate may be expedient.

Compounds which, under perhydrolysis conditions, result in aliphatic peroxocarboxylic acids having preferably 1 to 10 carbon atoms, in particular 2 to 4 carbon atoms, and/or optionally substituted perbenzoic acid, can be used as bleach activators. Substances that have O acyl and/or N acyl groups of the stated number of C atoms and/or optionally substituted benzoyl groups are suitable. Preferred are polyacylated alkylene diamines, in particular tetraacetylethylenediamine (TAED), acylated triazine derivatives, in particular 1,5-diacetyl-2,4-dioxo-hexahydro-1,3,5-triazine (DADHT), acylated glycolurils, in particular tetraacetylglycoluril (TAGU), N-acylimides, in particular N-nonanoyl succinimide (NOSI), acylated phenolsulfonates, in particular n-nonanoyl- or isononanoyloxybenzenesulfonate (n- or iso-NOBS), carboxylic acid anhydrides, in particular phthalic acid anhydride, acylated polyhydric alcohols, in particular triacetin, ethylene glycol diacetate, 2,5-diacetoxy-2,5-dihydrofuran and enol ester, and acetylated sorbitol and mannitol or mixtures thereof (SORMAN), acylated sugar derivatives, in particular pentaacetyl glucose (PAG), pentaacetyl fructose, tetraacetyl xylose and octaacetyl lactose, and acetylated, optionally N-alkylated glucamine and gluconolactone, and/or N-acylated lactams, for example N-benzoylcaprolactam. Hydrophilically substituted acyl acetals and acyl lactams are likewise preferably used. Combinations of conventional bleach activators can also be used. Bleach activators of this kind can be contained in a typical amount range, preferably in amounts of from 1 wt. % to 10 wt. %, in particular from 2 wt. % to 8 wt. %, based on the overall agent.

In addition to or instead of the conventional bleach activators listed above, sulfonimines and/or bleach-enhancing transition metal salts or transition metal complexes may also be contained as what are referred to as bleach catalysts.

Suitable as enzymes that can be used in the agents are those from the class of proteases, cutinases, amylases, pullulanases, hemicellulases, cellulases, lipases, oxidases and peroxidases, and mixtures thereof. Enzymatic active ingredients obtained from fungi or bacteria, such as *Bacillus subtilis, Bacillus licheniformis, Streptomyces griseus, Humicola lanuginosa, Humicola insolens, Pseudomonas pseudoalcaligenes* or *Pseudomonas cepacia* are particularly suitable. The optionally used enzymes can be adsorbed on carrier substances and/or embedded in coating substances to protect the enzymes from premature inactivation. The enzymes are, if desired, preferably contained in the agents according to the invention in amounts of no greater than 5 wt. %, in particular from 0.2 wt. % to 2 wt. %.

The agents can optionally contain, for example, derivatives of diaminostilbene disulfonic acid or alkali metal salts thereof as optical brighteners. Suitable are, for example, salts of 4,4'-bis(2-anilino-4-morpholino-1,3,5-triazinyl-6-amino)stilbene-2,2'-disulfonic acid or compounds having a similar structure which, instead of the morpholino group, have a diethanolamino group, a methylamino group, an anilino group or a 2-methoxyethylamino group.

Suitable foam inhibitors include, for example, organopolysiloxanes and mixtures thereof with microfine, optionally silanated silicic acid and paraffin waxes and mixtures thereof with silanated silicic acid or bis-fatty acid alkylene diamides. Mixtures of various foam inhibitors are also advantageously used, for example those made up of silicones, paraffins or waxes. The foam inhibitors, in particular silicone and/or paraffin-containing foam inhibitors, are preferably bonded to a granular carrier substance that is soluble or dispersible in water. Mixtures of paraffin waxes and bistearylethylenediamides are particularly preferred.

Furthermore, the agents can also contain components that positively influence the capability for washing out oil and grease from textiles, or what are referred to as soil-release active ingredients. This effect is particularly apparent when a textile is soiled which has been previously washed several times with an agent according to the invention that contains this oil and grease-dissolving component. Preferred oil and grease-dissolving components include, for example, non-ionic cellulose ethers such as methylcellulose and methylhydroxypropylcellulose with a proportion of from 15 to 30 wt. % of methoxyl groups and from 1 to 15 wt. % of hydroxypropoxyl groups, in each case based on the nonionic cellulose ether, and the polymers of phthalic acid and/or terephthalic acid, known from the prior art, or the derivatives thereof with monomeric and/or polymeric diols, in particular polymers of ethylene terephthalates and/or polyethylene glycol terephthalates or anionically and/or nonionically modified derivatives thereof.

The agents can also contain dye transfer inhibitors, preferably in amounts of from 0.1 wt. % to 2 wt. %, in particular from 0.1 wt. % to 1 wt. %, which, in a preferred embodiment of the invention, are polymers of vinylpyrrolidone, vinyl imidazole or vinyl pyridine-N-oxide or copolymers thereof.

The function of graying inhibitors is to keep the dirt that is removed from the textile fiber suspended in the liquor. Water-soluble colloids, which are usually organic, are suitable for this purpose, for example starch, sizing material, gelatin, salts of ethercarboxylic acids or ethersulfonic acids of starch or of cellulose, or salts of acidic sulfuric acid esters of cellulose or of starch. Water-soluble polyamides containing acidic groups are also suitable for this purpose. Starch derivatives other than those mentioned above may also be used, for example aldehyde starches. Cellulose ethers, such as carboxymethylcellulose (Na salt), methylcellulose, hydroxyalkylcellulose, and mixed ethers, such as methylhydroxyethylcellulose, methylhydroxypropylcellulose, methylcarboxymethylcellulose and mixtures thereof, can preferably be used, for example, in amounts of from 0.1 to 5 wt. %/o, based on the agents.

The organic solvents that can be used in the agents according to the invention, in particular when the agents are present in liquid or paste-like form, include alcohols having 1 to 4 carbon atoms, in particular methanol, ethanol, isopropanol, and tert-butanol, diols having 2 to 4 carbon atoms, in particular ethylene glycol and propylene glycol, and mixtures thereof, and the ethers that are derivable from the mentioned compound classes. Water-miscible solvents of this kind are preferably present in the agents according to the invention in amounts of no greater than 30 wt. %, in particular from 6 wt. % to 20 wt. %.

In order to set a desired pH that does not result automatically from mixing the other components, the agents according to the invention can contain acids that are compatible with the system and the environment, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium or alkali hydroxides. pH regulators of this kind are optionally contained in the agents according to the invention preferably in amounts of no greater than 20 wt. %, in particular from 1.2 wt. % to 17 wt. %.

The preparation of solid agents according to the invention (i.e. in particular washing or cleaning agents) poses no difficulties, and can be achieved in a manner which is known in principle, for example by spray drying or granulation, optional peroxygen compounds and optional bleach catalysts optionally being added separately at a later stage. For the preparation of agents according to the invention having an increased bulk weight, in particular in the range of from 650 g/l to 950 g/l, a method having an extrusion step is preferred. The preparation of liquid agents according to the invention also poses no difficulties, and may likewise be achieved in a known manner.

The preparation of the compounds of formula (I) according to the invention is described in the examples section by way of example, with reference to the preparation of a pro-fragrance containing undecan-2-one. The other compounds of general formulas (I), (II), (III) and (IV) may also be prepared via these basic synthesis routes.

According to a preferred embodiment, the teaching according to the invention can be used to significantly reduce the perfume proportion in washing, cleaning and body care agents. It is thus possible to also provide perfumed products for particularly sensitive consumers who, due to specific intolerances and irritations, can use the normally perfumed products only on a limited basis or not at all.

In various embodiments of the present invention, the washing or cleaning agents are present in liquid or in solid form.

A preferred solid, in particular powdered, washing agent according to the invention can also contain, in addition to the compound according to the invention, in particular components that are selected from the following, for example:

anionic surfactants, such as preferably alkylbenzenesulfonate, alkyl sulfate, e.g. in amounts of preferably from 5 to 30 wt. %, nonionic surfactants, such as preferably fatty alcohol polyglycol ether, alkyl polyglucoside, fatty acid glucamide, e.g. in amounts of preferably from 0.5 to 15 wt. %, builders, for example zeolite, polycarboxylate, sodium citrate, in amounts of e.g. from 0 to 70 wt. %, advantageously from 5 to 60 wt. %, preferably from 10 to 55 wt. %, in particular from 15 to 40 wt. %, alkalis, for example sodium carbonate, in amounts of e.g. from 0 to 35 wt. %, advantageously from 1 to 30 wt. %, preferably from 2 to 25 wt. %, in particular from 5 to 20 wt. %, bleaching agents, for example sodium perborate, sodium percarbonate, in amounts of e.g. from 0 to 30 wt. %, advantageously from 5 to 25 wt. %, preferably from 10 to 20 wt. %, corrosion inhibitors, e.g. sodium silicate, in amounts of e.g. from 0 to 10 wt. %, advantageously from 1 to 6 wt. %, preferably from 2 to 5 wt. %, in particular from 3 to 4 wt. %, stabilizers, e.g. phosphonates, advantageously from 0 to 1 wt. %, foam inhibitors, e.g. soap, silicone oils, paraffins, advantageously from 0 to 4 wt. %, preferably from 0.1 to 3 wt. %, in particular from 0.2 to 1 wt. %, enzymes, e.g. proteases, amylases, cellulases, lipases, advantageously from 0 to 2 wt. %, preferably from 0.2 to 1 wt. %, in particular from 0.3 to 0.8 wt. %, graying inhibitors, e.g. carboxymethylcellulose, advantageously from 0 to 1 wt. %, discoloration inhibitors, e.g. polyvinylpyrrolidone derivatives, preferably from 0 to 2 wt. %, adjusters, e.g. sodium sulfate, advantageously from 0 to 20 wt. %, optical brighteners, e.g. stilbene derivatives, biphenyl derivatives, advantageously from 0 to 0.4 wt. %, in particular from 0.1 to 0.3 wt. %, optionally further fragrances,
optionally water,
optionally soap,
optionally bleach activators,
optionally cellulose derivatives,
optionally soil-repellent agents, given in wt. %, in each case based on the overall agent.

In another preferred embodiment of the invention, the agent is present in liquid form, preferably in gel form. Preferred liquid washing or cleaning agents and cosmetics have water contents of e.g. from 10 to 95 wt. %, preferably from 20 to 80 wt. %, and in particular from 30 to 70 wt. %, based on the overall agent. In the case of liquid concentrates, the water content can also be particularly low, for example <30 wt. %, preferably <20 wt. %, in particular <15 wt. %, in wt. % in each case based on the overall agent. The liquid agents may also contain non-aqueous solvents.

A preferred liquid, in particular gel, washing agent according to the invention can also contain, in addition to the compound according to the invention, in particular components that are selected from the following, for example:

anionic surfactants, such as preferably alkylbenzenesulfonate, alkyl sulfate, e.g. in amounts of preferably from 5 to 40 wt. %, nonionic surfactants, such as preferably fatty alcohol polyglycol ether, alkyl polyglucoside, fatty acid glucamide, e.g. in amounts of preferably from 0.5 to 25 wt. %, builders, for example zeolite, polycarboxylate, sodium citrate, advantageously from 0 to 15 wt. %, preferably from 0.01 to 10 wt. %, in particular from 0.1 to 5 wt. %, foam inhibitors, e.g. soap, silicone oils, paraffins, in amounts of e.g. from 0 to 10 wt. %, advantageously from 0.1 to 4 wt. %, preferably from 0.2 to 2 wt. %, in particular from 1 to 3 wt. %, enzymes, e.g. proteases, amylases, cellulases, lipases, in amounts of e.g. from 0 to 3 wt. %, advantageously from 0.1 to 2 wt. %, preferably from 0.2 to 1 wt. %, in particular from 0.3 to 0.8 wt. %, optical brighteners, e.g. stilbene derivatives, biphenyl derivatives, in amounts of e.g. from 0 to 1 wt. %, advantageously from 0.1 to 0.3 wt. %, in particular from 0.1 to 0.4 wt. %, optionally further fragrances,
optionally stabilizers,
water optionally soap, in amounts of e.g. from 0 to 25 wt. %, advantageously from 1 to 20 wt. %, preferably from 2 to 15 wt. %, in particular from 5 to 10 wt. %, optionally solvents (preferably alcohols), advantageously from 0 to 25 wt. %, preferably from 1 to 20 wt. %, in particular from 2 to 15 wt. %, given in wt. %, in each case based on the overall agent.

A preferred liquid softener according to the invention can also contain, in addition to the ketone according to the invention, in particular components that are selected from the following:

cationic surfactants, such as in particular esterquats, e.g. in amounts of from 5 to 30 wt. %, cosurfactants, for example glycerol monostearate, stearic acid, fatty alcohols, fatty alcohol ethoxylates, e.g. in amounts of from 0 to 5 wt. %, preferably from 0.1 to 4 wt. %, emulsifiers, for example fatty amine ethoxylates, e.g. in amounts of from 0 to 4 wt. %, preferably from 0.1 to 3 wt. %, optionally further fragrances,
dyes, preferably in the ppm range,
stabilizers, preferably in the ppm range,
solvents, for example water, in amounts of preferably from 60 to 90 wt. %, given in wt. %, in each case based on the overall agent.

A further subject of the invention is a method for long-lastingly fragrancing surfaces, a compound according to the invention of general formula (I) or a washing or cleaning agent, cosmetic agent or air care agent according to the invention being applied to the surface to be fragranced (e.g. textiles, dishes, floors), and said surface then being exposed to conditions which provide for hydrolysis of the pro-fragrance.

EXAMPLES

Example 1: Synthesis of Undecanone Based on L-(−)-Sorbose

Stage 1: 2,2-dimethoxyundecane

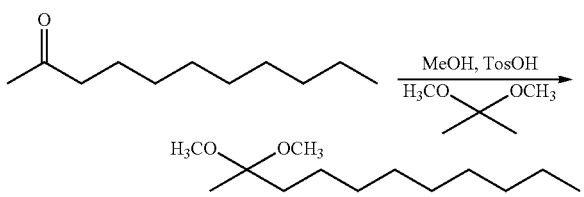

Toluene-4-sulfonic acid (1.90 g, 10 mmol) was repeatedly heated and argon was repeatedly added thereto in a 500 ml Schlenk flask under a vacuum (approx. 0.1 mbar). Methanol (80 ml) and 2,2-dimethoxypropane (208.3 g, 2.0 mol) was then added through a septum stopper. Then, the reaction mixture was cooled to approximately −50° C. and undecan-2-one (17.0 g, 100 mmol) was added drop by drop. The mixture was stirred at −50° C. for four hours, and then cooling was stopped and the mixture was heated to room temperature overnight. After being heated to 50° C., the reaction mixture was stirred at this temperature for a further 7 hours. The mixture cooled to room temperature was reprocessed by diethyl ether (300 ml) being added, by being washed twice with cold saturated NaHCO$_3$ solution and washed once with saturated NaCl solution, by the organic phase being dried using MgSO$_4$, by being filtered and by being concentrated on a rotary evaporator. 18.1 g (product: 13.5 g, 62.6 mmol, 63%) of a yellow, clear oil was obtained (2,2-dimethoxyundecane:undecanone; 7:3).

Stage 2: Undecanone Based on L-(−)-Sorbose

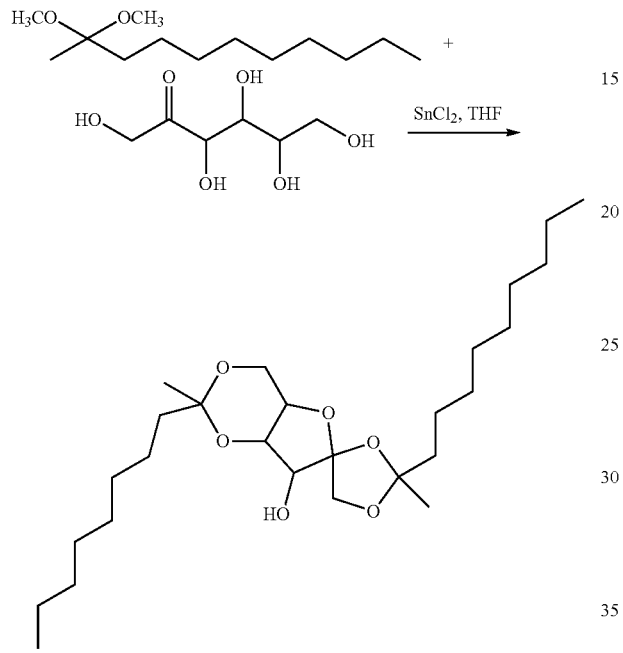

2,2-dimethoxyundecane (2.61 g, 12.1 mmol) in a mixture with undecanone (2.88 g, 16.9 mmol) was dissolved in 10 ml of THF, L-(−)-sorbose (1.14 g, 6.34 mmol) and zinc(II) chloride (11.0 mg, 59.0 µmol) was added in the argon counterflow, and the mixture was stirred at 70° C. for 41 hours. The suspension cooled to room temperature was filtered through a frit after triethylamine (30 µl) was added and after being stirred for a short period of time and then the filtrate was concentrated under reduced pressure. After purification by column chromatography (pentane:ethyl acetate gradient 95:5 to 70:30 with 1% triethylamine), two product fractions were obtained (isomer 1: 210 mg, 433 µmol; isomer 2: 430 mg, 888 µmol, yield 21%).

Example 2: Release Behavior

The test substances were dissolved in diethyl ether in equal molar amount compared with the odorant contained therein and then pipetted onto a fragrance smelling strip. The smelling strip treated in this manner was then stored at room temperature and the intensity of the fragrance was assessed by smell and rated on a scale of 1 to 10 (10=intense odor, 0=no odor). In order to evaluate boost effects, the test strips were sprayed with an aqueous pH buffer system at various points in time and subsequently likewise assessed by smell. Isomer 1, which was obtained in stage 2 of example 1, was the subject of tests.

|  | in diethyl ether for 0 minutes | 30 minutes | 30 minutes and spraying | 60 minutes | 60 minutes and spraying |
|---|---|---|---|---|---|
| Isomer 1 0.2 mmol/ml | 4 | 3 | 4 to 5 | 2 | 3 |
| Undecanone 0.2 mmol/ml | 6 | 4 | 4 | 1 | 1 |

What is claimed is:

1. A compound having the structure:

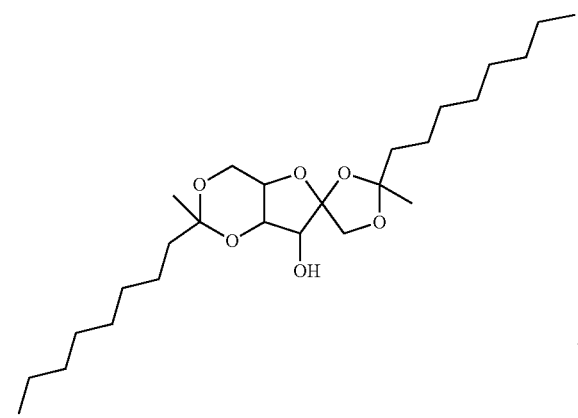 [SMILES: CCCCCCCCC1(C)OCC2OC3(COC(C)(CCCCCCCC)O3)C(O)C2O1]

2. A washing or cleaning agent comprising:
a. the following compound:

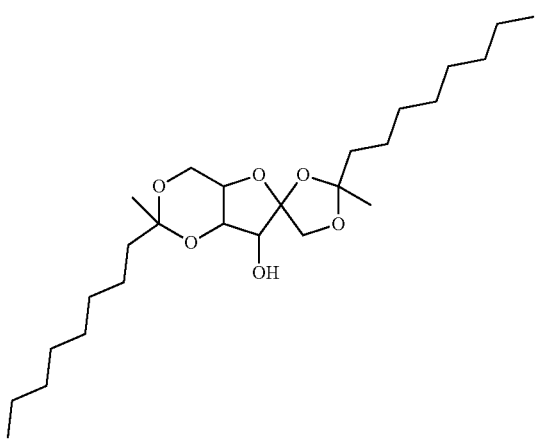 [SMILES: CCCCCCCCC1(C)OCC2OC3(COC(C)(CCCCCCCC)O3)C(O)C2O1]

that is present in an amount of from 0.0001 and 5 wt. % based on the overall agent, and b. at least one surfactant selected from the group consisting of anionic, cationic, nonionic, zwitterionic, amphoteric surfactants and mixtures thereof, and c. the washing or cleaning agent is present in liquid or solid form.

3. An insect repellent composition including:
an insect repellant; and
the following compound:

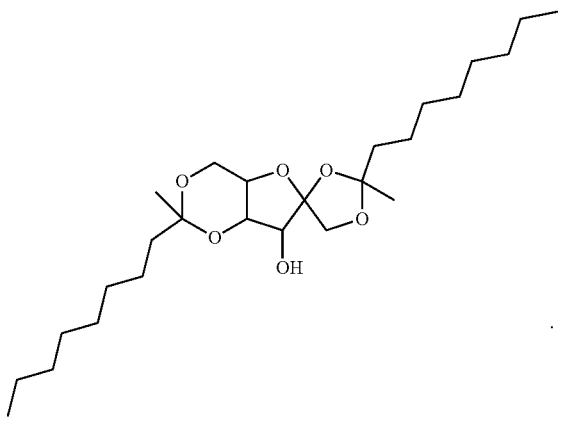 [SMILES: CCCCCCCCC1(C)OCC2OC3(COC(C)(CCCCCCCC)O3)C(O)C2O1]

4. The washing or cleaning agent according to claim 2, wherein the compound is included in an amount of from 0.001 to 4 wt. % based on the overall agent.

5. The insect repellant composition of claim 3 wherein the compound is included in an amount of from 0.001 to 50 wt. % based on the weight of the composition.

6. The washing or cleaning agent of claim 2 that is solid and comprises:

an anionic surfactant in an amount of from 5 to 30 wt. %,
a nonionic surfactant in an amount of from 0.5 to 15 wt. %,
a builder in an amount of from 5 to 60 wt. %,
an alkali in an amount of from 1 to 30 wt. %,
a bleaching agent in an amount of from 5 to 25 wt. %,
a corrosion inhibitor in an amount of 1 to 6 wt. %,
a stabilizer in an amount of from 0 to 1 wt. %, and
a foam inhibitor in an amount of 0.1 to 3 wt. %,
wherein each amount is based on a total weight of the agent.

7. The washing or cleaning agent of claim 6 that is a powder.

8. The washing or cleaning agent of claim 2 that is liquid and comprises:

an anionic surfactant in an amount of from 5 to 40 wt. %,
a nonionic surfactant in an amount of from 0.5 to 25 wt. %,
a builder in an amount of from 0.01 to 10 wt. %, and
a foam inhibitor in an amount of 0.1 to 4 wt. %,
wherein each amount is based on a total weight of the agent.

9. The washing or cleaning agent of claim 8 that is a gel.

* * * * *